(12) United States Patent
Fanti

(10) Patent No.: US 6,964,654 B2
(45) Date of Patent: Nov. 15, 2005

(54) DISPOSABLE COVER FOR DRAINABLE STOMA POUCH

(76) Inventor: Roy Fanti, 171 Atwater Rd., Springfield, MA (US) 01107

(*) Notice: Subject to any disclaimer, the term of this patent is extended or adjusted under 35 U.S.C. 154(b) by 252 days.

(21) Appl. No.: 10/178,408

(22) Filed: Jun. 25, 2002

(65) Prior Publication Data

US 2003/0191441 A1    Oct. 9, 2003

Related U.S. Application Data

(60) Provisional application No. 60/370,694, filed on Apr. 9, 2002.

(51) Int. Cl.$^7$ .................................................. A61F 5/44
(52) U.S. Cl. .................................... 604/333; 604/335
(58) Field of Search ............................... 604/332–345, 604/355; 24/30.5 R

(56) References Cited

U.S. PATENT DOCUMENTS

| | | | |
|---|---|---|---|
| 3,825,005 A * | 7/1974 | Fenton ........................ | 604/335 |
| 4,203,445 A | 5/1980 | Jessup et al. | |
| 4,349,104 A | 9/1982 | Hayes | |
| 4,387,713 A * | 6/1983 | Calanni ........................ | 604/333 |
| 4,439,191 A * | 3/1984 | Hogan ........................ | 604/332 |
| 4,465,486 A * | 8/1984 | Hill ............................ | 604/337 |
| 4,516,974 A | 5/1985 | Davis | |
| 4,705,512 A * | 11/1987 | Faucher ....................... | 604/332 |
| 5,009,828 A | 4/1991 | McCree | |
| 5,070,584 A | 12/1991 | Dais et al. | |
| 5,647,100 A | 7/1997 | Porchia et al. | |
| 5,690,621 A | 11/1997 | Canela | |
| 5,707,696 A | 1/1998 | Boxler | |
| 6,022,144 A * | 2/2000 | Hausslein .................... | 383/33 |

* cited by examiner

Primary Examiner—Larry I. Schwartz
Assistant Examiner—C. Lynne Anderson
(74) Attorney, Agent, or Firm—Jacobson Holman PLLC

(57) ABSTRACT

A disposable cover for enclosing the outlet spout of a drainable stoma pouch. The cover includes front and rear walls sealed along side and bottom edges, with an unsealed upper edge. Preferably, one or more stiffening ribs extend longitudinally across the front and rear walls near the unsealed upper edge. The presence, spacing and relative orientation of such ribs on the external surfaces of the front and rear walls render the disposable cover self-opening such that it may be easily placed over to enclose the outlet spout of a drainable stoma pouch. Once positioned, the cover is clamped onto the tail section of the pouch to provide effective odor and moisture containment therein.

22 Claims, 4 Drawing Sheets

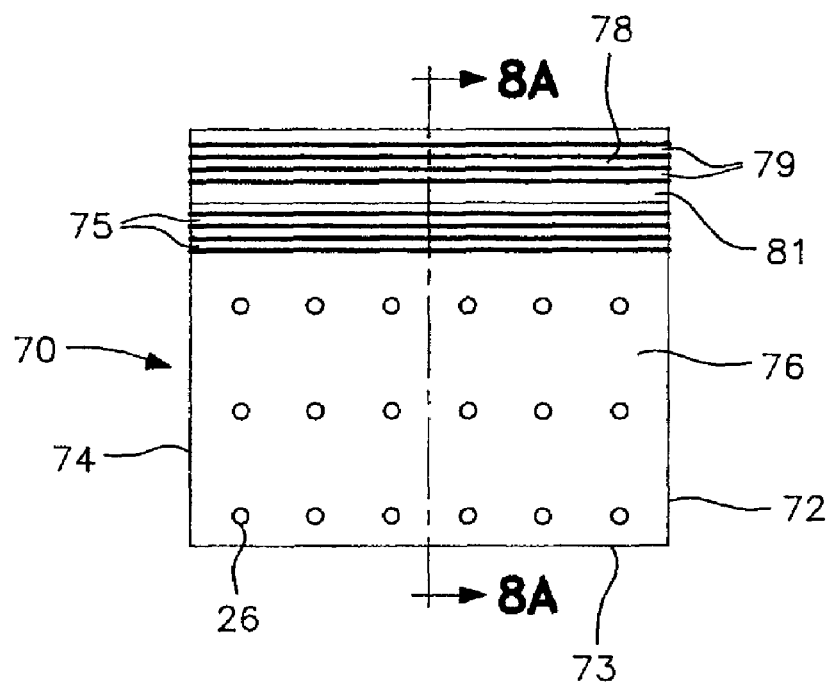
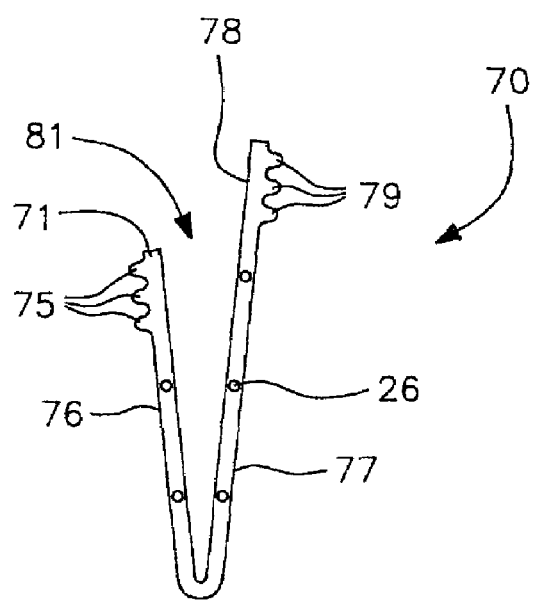
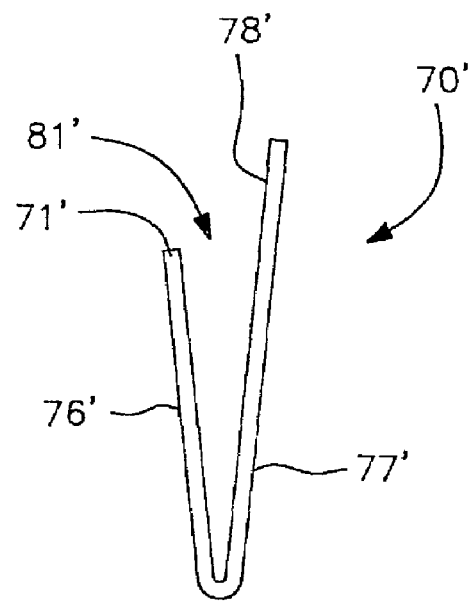

DISPOSABLE COVER FOR DRAINABLE STOMA POUCH

This application claims priority from and the benefit of prior provisional application, Ser. No. 60/370,694 with filing date of Apr. 9, 2002.

BACKGROUND OF THE INVENTION

1. Field of the Invention

The present invention relates generally to drainable stoma pouches and, more particularly, to a disposable device for covering the outlet spout of a drainable stoma pouch.

2. Description of the Related Art

Many varieties of drainable stoma pouches exist for use by the hundreds of thousands of patients requiring these devices due to ostomy surgery. The pouches include an outlet spout and, when the pouch is sufficiently full, it is necessary to drain the contents through such spout. A clamp is typically provided for use as the only means to seal off the excretion of residual feces particles from the outlet following drainage. Present drainable pouches and the means for emptying the same do not adequately manage the problems inherent in handling the waste products involved. More particularly, there is no cover or other mechanism provided to enclose the open outlet of the pouch, through which the waste product of the patient is excreted, in between drainage operations.

U.S. Pat. No. 5,690,621 discloses a system in which the drainable pouch is washed to remove the waste products contained therein, providing a cap for the pouch outlet that is attached to the pouch with a strap and hook connection so that the cap becomes a permanent and integral part of the pouch design. The pouch is not disposable, scented or self-opening.

U.S. Pat. No. 5,707,696 teaches a method for manufacture of scented plastic materials, and U.S. Pat. No. 4,349,104 provides for scented bags for disposal of odorous materials. Neither reference suggests a self-opening, disposable cover suitable for use with a drainable stoma pouch.

U.S. Pat. Nos. 5,009,828, 5,647,100 and 5,070,584 are representative of prior art zippers for a recloseable thermoplastic bag having internal rib and groove profiles, and methods for their fabrication. The internal rib and groove profiles are specially located and designed to ensure bag closure, but do not teach or provide for a self-opening feature.

Finally, U.S. Pat. Nos. 4,516,974 and 4,203,445 are directed to a gas venting device integrated within a more complex stoma pouch. This device does not offer hygienic simplicity or easily obtained gas venting effectiveness.

Accordingly, a need exists for an effective covering device that is low in cost, so as to be disposable, preferably self-opening for ease of use, and effective for containing odors and fluids resident within the outlet of a drainable stoma pouch.

SUMMARY OF THE INVENTION

In view of the shortcomings of the prior art, the present invention is directed to a disposable cover for enclosing the outlet spout of a drainable stoma pouch. The cover includes front and rear walls sealed along side and bottom edges, with an unsealed upper edge. One or more stiffening ribs may extend longitudinally across at least a portion of the front and rear walls near the unsealed upper edge, in either an opposing or vertically displaced arrangement. When ribs are included, the spacing and relative orientation of such ribs on the external surfaces of the front and rear walls render the cover self-opening so that it may be easily placed over to enclose the outlet spout of a drainable stoma pouch. Once positioned, the cover is clamped onto the tail section of the pouch to provide effective odor and moisture containment therein.

Accordingly, it is an object of the present invention to overcome the difficulties of containing fluids and odors between drainage operations of a stoma pouch.

Another object of the present invention is to provide a disposable cover for a drainable stoma pouch that may be cost-effectively discarded following a single use.

A further object of the present invention is to provide a cover for the open end of a drainable stoma pouch that is self-opening and thus easy to use, allowing colostomy patients to contain or eliminate unwanted odors, gases and waste matter conditions associated with an uncovered stoma pouch outlet.

Yet another object of the present invention is to provide a self-opening cover for a stoma pouch that is scented to improve odor management.

Still a further object of the present invention is to provide a cover for a stoma pouch that significantly reduces the psychological and emotional stresses colostomy patients endure when coping with the drainage operations associated with existing drainable stoma pouches.

These together with other objects and advantages which will become subsequently apparent reside in the details of construction and operation as more fully hereinafter described and claimed, reference being had to the accompanying drawings forming a part hereof, wherein like numerals refer to like parts throughout.

BRIEF DESCRIPTION OF THE DRAWINGS

FIG. 7 is a front view of a cover in accordance with a fourth preferred embodiment of the present invention;

FIG. 8A is a side cross-sectional view taken along line 8A—8A of FIG. 7; and

FIG. 8B is a side cross-sectional view of a disposable cover useable like that shown in FIG. 7 but without ribs or fragrance components.

DETAILED DESCRIPTION OF THE PREFERRED EMBODIMENTS

Figure 1:
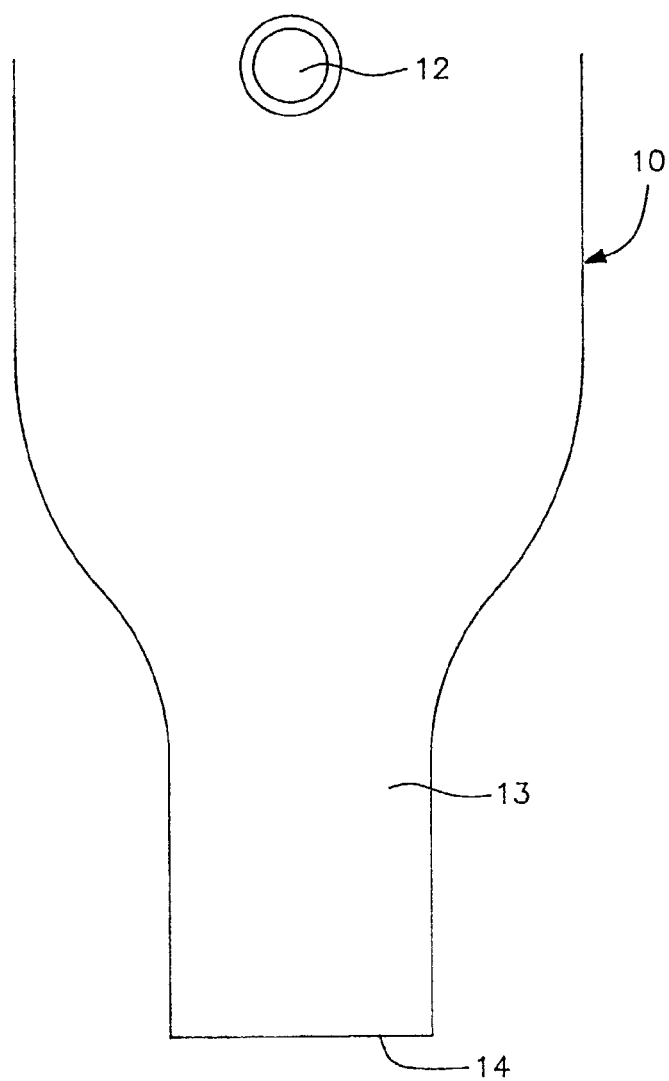
FIG. 1 is a front view of a first preferred embodiment of a disposable, scented cover, as it appears when ready to be affixed to a drainable stoma pouch, in accordance with the present invention.

In describing preferred embodiments of the invention illustrated in the drawings, specific terminology will be resorted to for the sake of clarity. However, the invention is not intended to be limited to the specific terms so selected, and it is to be understood that each specific term includes all technical equivalents which operate in a similar manner to accomplish a similar purpose.

Figure 2A:
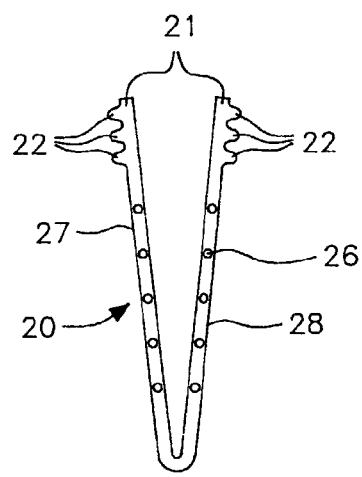
FIG. 2A is a side cross-sectional view taken along line 2A—2A of FIG. 1.

As shown in FIGS. 1 and 2A, the present invention is directed to a self-opening cover, generally designated by the reference numeral 20, to be used to cover the outlet spout 14 of a drainable stoma pouch, generally designated by the reference numeral 10. The stoma pouch 10 may be one of a number of stoma pouch designs that include a stoma opening 12 and a tail section 13 in which the pouch narrows down toward the outlet spout 14. In FIG. 1, the cover 20 is shown as separated from the pouch 10, but is depicted in a position where it may be readily placed over the spout 14 through movement of the cover 20 in the direction indicated by the arrows 19.

The self-opening cover 20 is formed of two generally rectangular walls 27, 28 having two sealed side edges 23, 25, an unsealed top edge 21, and a sealed bottom edge 24. Alternatively, as shown in the side cross-sectional view of FIG. 2A, the cover may be a single piece of material folded along the bottom edge 24 and sealed along side edges 23, 25. In another alternative, the cover may be constructed of tubular material, without side seams, having a sealed bottom edge.

The walls have a generally smooth interior surface and may be made of any suitable thermoplastic or other plastic or non-plastic material which is impermeable to moisture; such materials are commercially available as is known by persons of ordinary skill in the art. Embedded within, sprayed upon or otherwise attached to or integral with the walls are one or more fragrance elements 26.

In the vicinity of the top edges 21, one or more ridges or stiffening ribs 22 are provided that, in the embodiment shown in FIGS. 1 and 2A, extend substantially from one side edge 23 to the other side edge 25; ribs extending only partially across one or both walls may also be effectively employed. The ribs 22 are generally parallel with one another and with the top edges 21 and, as shown in FIG. 2A, are external to the walls 27, 28, with the ribs on one wall opposing the ribs on the other wall. The ribs 22 are made of a suitable plastic, polymer or rubber-type material and are prestressed with an outward bowing curvature such that, when such ribs are attached to the external surfaces of the walls 27, 28, the unsealed edges 21 are self-opening, controlled essentially by the amount of prestressing of the ribs 22.

Figure 2B:
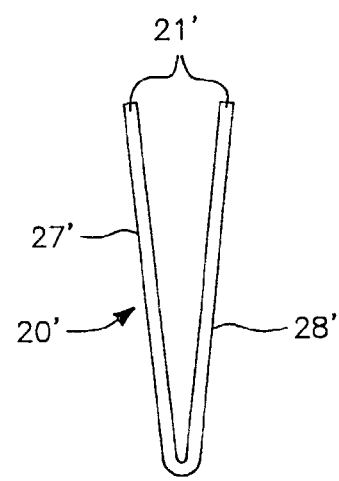
FIG. 2B is a side cross-sectional view of a disposable cover useable like that shown in FIG. 1 but without ribs or fragrance components.

Alternatively, the disposable cover according to the present invention may be constructed without ribs and/or without fragrance elements, as shown in FIG. 2B. As with the cover shown in FIG. 2A, the disposable cover, generally designated by the reference numeral 20', is formed of two generally rectangular walls 27', 28' which may be sealed or integrally formed with one another along the bottom and sides thereof, in the same manner already set forth in connection with the self-opening embodiment shown in FIGS. 1 and 2A. The cover 20' has unsealed top edge 21' for fitting over the outlet spout 14. While lacking the true self-opening capability provided by the ribs, the cover 20' is still effective in use and may be handled without difficulty by those having sufficient manual dexterity. Such a cover is very easily manufactured and low in cost, rendering it highly disposable and easing the user's mind relative to the frequency with which the cover is changed.

Figure 3:
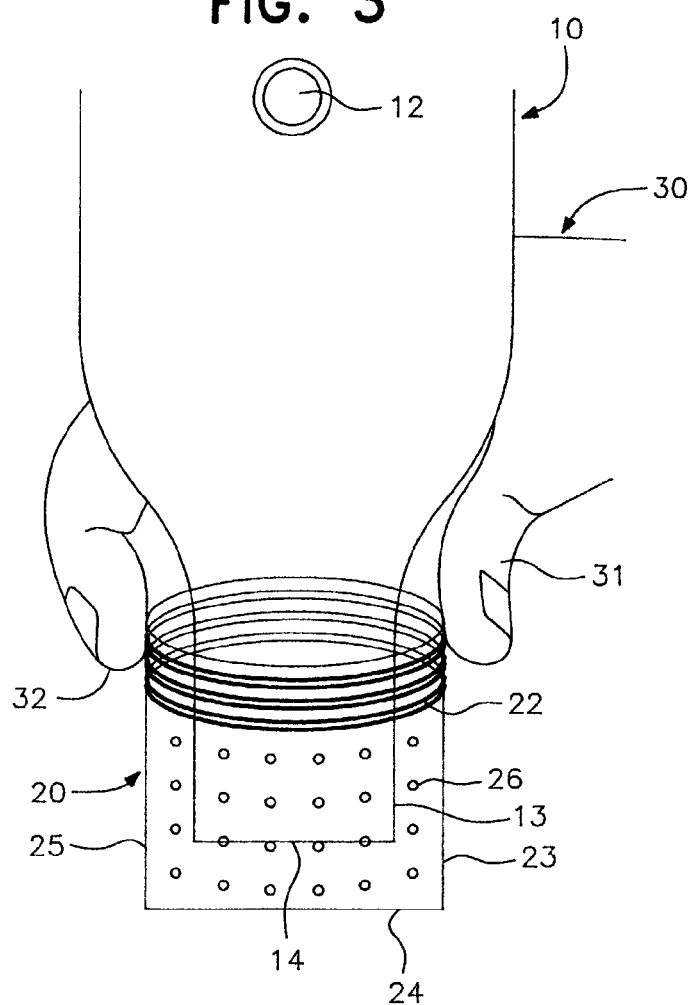
FIG. 3 is an isometric view of the disposable scented cover of FIG. 1, as placed over the open outlet of the drainable stoma pouch and onto the tail section.
Figure 4:
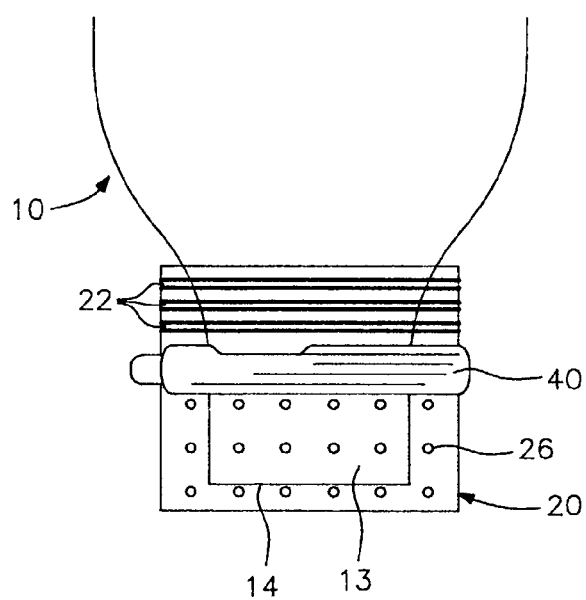
FIG. 4 is a partial front view illustrating the disposable cover of FIG. 1 clamped onto the tail section of the stoma pouch.

FIG. 3 illustrates use of the invention and the ease with which a user can grip the tops of side edges 23, 25, with the thumb 31 and forefinger 32 of hand 30, along the ribs 22 and, by exerting inward pressure to more widely open the unsealed edges, position the cover 20 over the tail section 13 and outlet spout 14 of the pouch 10. The cover is moved upwardly, relative to the stoma opening 12, until the tail section extends below the ribs. Once the cover is positioned as shown in FIG. 3, the walls of the cover are pressed against the tail section 13 using an external, self-locking clamping device 40, as shown in FIG. 4. The clamping device 40 is positioned below the ribs 22, or in a comparable location if using the cover shown in FIG. 2B, and serves not only to seal the lower portion of the pouch above the spout 14, but also to trap any liquid and/or odors resident in the spout within the moisture impermeable cover 20, 20'. The clamping device 40 may be any suitable element that provides compression across the full width of the cover and stoma tail section. For purposes herein, the width of the cover is considered to be the distance from one side edge to the other side edge.

Figure 5A:
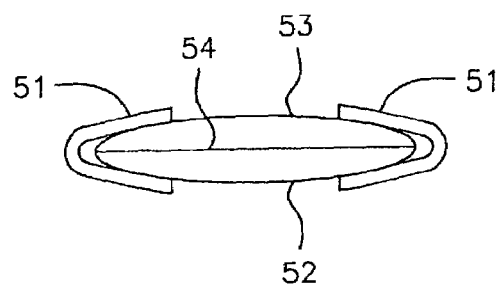
FIG. 5A is a top view of a cover in accordance with a second preferred embodiment of the present invention.
Figure 5B:
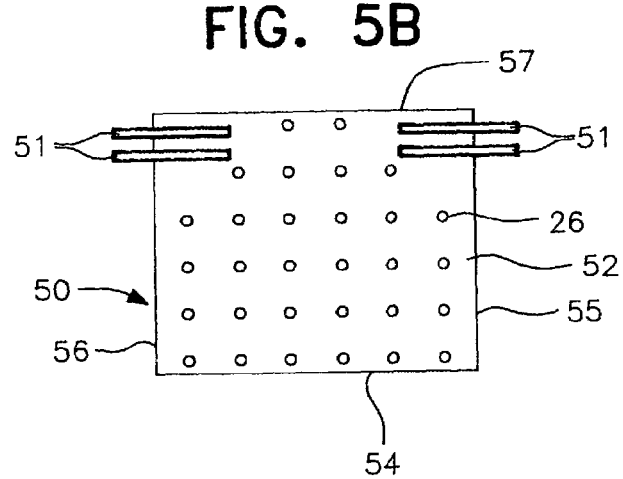
FIG. 5B is a front view of the cover of FIG. 5A.

A second embodiment of the cover of the present invention, generally designated by the reference numeral 50, is depicted in FIGS. 5A and 5B. The cover 50 includes front and rear walls 52, 53 joined by sealed or unitary side edges 55, 56 and either a sealed or unitary bottom edge 54. Fragrance components 26 are preferably incorporated in at least one wall 52, 53.

In this embodiment, externally placed side ribs 51 extend from one wall 52 to the other wall 53 so as to loop over the side edges 55, 56, but the ribs do not extend longitudinally across the full width of the walls. As with the embodiment of FIGS. 1–4, the ribs are positioned in the vicinity of the unsealed edges 57. The looping arrangement coupled with the external spacing and positioning of the ribs 51 causes an outward bowing stress on the ribs 51 which results in an automatic self-opening posture, spreading the front and rear walls 52, 53 apart from one another adjacent top edges 57. Again, once positioned over the tail section 13 of the pouch 10 above the spout 14, a suitable clamp 40 secures the cover 50 in position.

Figure 6A:
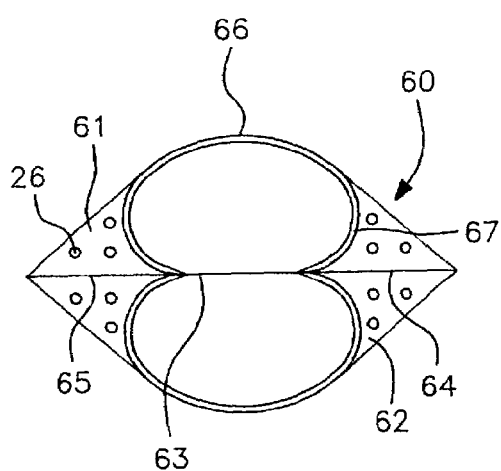
FIG. 6A is a top view of a cover in accordance with a third preferred embodiment of the present invention.
Figure 6B:
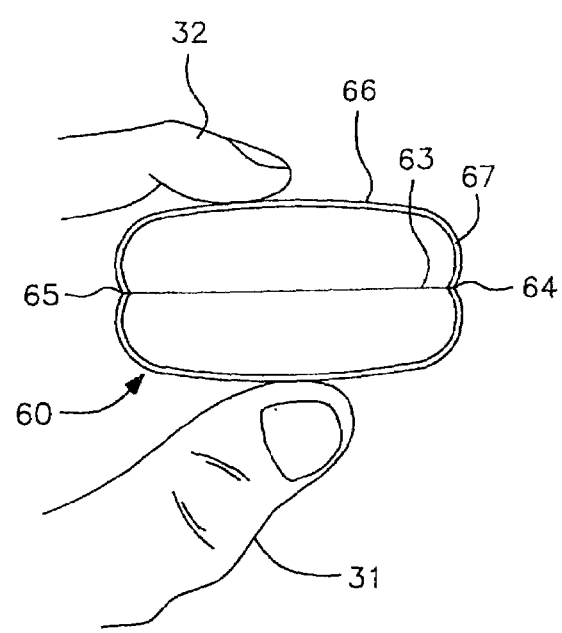
FIG. 6B depicts a top isometric view of the cover of FIG. 6A, shown compressed by a user's thumb and forefinger.

A third embodiment of the present invention is shown in FIGS. 6A and 6B. The cover, generally designated by the reference numeral 60, includes walls 61, 62 joined by sealed or unitary side edges 64, 65 and either a sealed or unitary bottom edge 63. Fragrance components 26 are preferably incorporated in at least one wall 61, 62.

In this embodiment, at least one rib 67 is provided adjacent and generally parallel with the unsealed top edge 66. During construction of the cover 60, the rib is preferably formed integrally on the inner surface of walls 61, 62, in a manner analogous to that used in constructing Ziplock® bags. Then, the walls 61, 62, which are already joined along edges 64, 65, are turned inside-out so that the rib 67 is on the external surface thereof, the natural bow thereof springing the unsealed top edge 66 into an open position, as shown in top view in FIG. 6A. By squeezing the walls toward one another through pressure along the rib 67, as shown in FIG. 6B, the user can broaden the width of the cover's unsealed edge 66 to accommodate the width of the outlet spout 14. Once the spout is inserted into the cover 60 to a sufficient depth, the cover is secured to the tail section 13 with a suitable clamping device 40, as shown in FIG. 4.

A fourth embodiment of the cover, generally designated by the reference numeral 70, is illustrated in FIGS. 7 and 8A. The cover 70 includes front and rear walls 76, 77 joined by sealed or unitary side edges 72, 74 and either a sealed or unitary bottom edge 73, and preferably fragrance components 26. The rear wall 77 includes a lip region 78 that extends the height of the rear wall above the unsealed edge 71 of the front wall 76. This lip region 78 projects beyond the unsealed edge 71 preferably one inch or less.

In this fourth embodiment, a first set of ribs 75 extends substantially from one side edge 72 to the other side edge 74 along the front wall 76. A second set of ribs 79 extends substantially from one side edge 72 to the other side edge 74 along the lip region 78 of the rear wall 77. The first and second sets of ribs 75, 79 are generally parallel with one another and external to the walls 76, 77 but, unlike the first embodiment, are vertically displaced. The ribs are prestressed with an outward bowing curvature such that, when such ribs are attached to the external surfaces of the walls 76, 77, the unsealed opening 81 defined by the edge 71 and the lip region 78 is self-opening. As with the previous embodiments, the ribs are positioned in the vicinity of the unsealed opening 81, with the first set of ribs 75 positioned just below the opening, and the second set of ribs 79 positioned just above the opening 81. While shown extending over the entire length of the opening 81, the lip region 78 may be constructed to extend over only a portion of such opening.

Alternatively, the disposable cover according to the present invention may be constructed without ribs and/or without fragrance elements, as shown in FIG. 8B. As with the cover shown in FIG. 8A, the disposable cover, generally designated by the reference numeral 70', is formed of two generally rectangular walls 76', 77' which may be sealed or integrally formed with one another along the bottom and sides thereof, in the same manner already set forth in connection with the self-opening embodiment shown in FIGS. 7 and 8A. The cover 70' has unsealed top edge 71' and lip region 78' defining opening 81' for fitting over the outlet spout 14. While lacking the true self-opening capability provided by the ribs, the cover 70' is still effective in use and may be handled without difficulty by those having sufficient manual dexterity. Such a cover is very easily manufactured and low in cost, rendering it highly disposable and easing the user's mind relative to the frequency with which the cover is changed.

In use, the covers 70, 70' are opened and positioned in the same way as that shown in FIG. 3, and thereafter clamped as shown in FIG. 4.

The embodiments disclosed herein generally depict one, two and three ribs on each wall, since any number of ribs may be suitably employed in each of the embodiments. Positioning of the ribs on the external surfaces of the walls, regardless of the number of ribs, renders the resulting cover self-opening, greatly facilitating ease of use of the cover for its intended purpose. Furthermore, the ribs may be integrally formed with the walls of the cover or may be adhered to the walls using an adhesive or other suitable affixing mechanism. Alternatively, the cover may be manufactured without ribs as has already been discussed.

The design of the inventive covers as described herein also enables the user to easily control the venting of gases that may collect in the cover without even having to remove the cover. The user can choose, whenever desired or convenient, to release the clamp and, with the cover still enclosing the outlet spout but not clamped thereto, the user may press the walls of the bag inwardly toward one another to reduce the volume contained within the cover and thereby expel gases through the unsealed upper edges thereof. The clamp may then be re-secured to seal the walls of the cover against one another for continued use of the same cover.

The foregoing descriptions and drawings should be considered as illustrative only of the principles of the invention. The invention may be configured in a variety of shapes and sizes and is not limited to the specific embodiments set forth herein. Therefore, it is not desired to limit the invention to the specific examples disclosed or the exact construction and operation shown and described. Rather, all suitable modifications and equivalents may be resorted to, falling within the scope of the invention.

What is claimed is:

1. A disposable cover having an external, self-locking clamping device in combination with a drainable stoma pouch, said cover comprising a front wall and a rear wall joined along respective bottom and side edges, unsealed upper edges of said walls defining an opening for receiving an outlet spout of a stoma pouch, said external, self-locking clamping device securing the walls of said cover to said stoma pouch following insertion of an outlet spout within said opening by sealingly pressing said front and rear walls of said cover against one another with said stoma pouch sandwiched therebetween across a full width thereof and without folding of either said stoma pouch or said cover to thereby seal a lower portion of said pouch above said outlet spout with said clamping device locked thereon and prevent escape of stoma pouch contents during regular use of the pouch by a stoma patient to collect discharge from the stoma within the pouch, said cover, when so secured to the stoma pouch, trapping any liquid or gases resident in said outlet spout beneath said clamping device.

2. The cover as set forth in claim 1, further comprising at least one rib on an external surface of each of said front and rear walls, said ribs extending substantially parallel with and adjacent said unsealed upper edges and being prestressed with an outward bowing curvature such that said upper edges are self-opening, facilitating placement of said outlet spout within said opening, said ribs remaining separated from one another when the pouch is closed by clamping of the cover thereagainst.

3. The cover as set forth in claim 2, wherein said at least one rib on said front wall is opposed to said at least one rib on said rear wall.

4. The cover as set forth in claim 2, wherein said at least one rib on said front wall is vertically displaced relative to said at least one rib on said rear wall.

5. The cover as set forth in claim 4, wherein said rear wall includes a lip portion extending above at least a portion of the unsealed upper edge of said front wall, said at least one rib on said rear wall being affixed to said lip portion.

6. The cover as set forth in claim 1, wherein at least one of said front wall and said rear wall includes a fragrance element.

7. The cover as set forth in claim 2, wherein said front wall includes a first plurality of ribs and said rear wall includes a second plurality of ribs.

8. The cover as set forth in claim 7, wherein said first plurality of ribs is opposed to said second plurality of ribs.

9. The cover as set forth in claim 7, wherein said first plurality of ribs is vertically displaced relative to said second plurality of ribs.

10. The cover as set forth in claim 9, wherein said rear wall includes a lip portion extending above at least a portion of the unsealed upper edge of said front wall, said second plurality of ribs being affixed to said lip portion.

11. The cover as set forth in claim 2, wherein said ribs loop over the side edges to extend from the front wall to the rear wall, thereby causing the unsealed upper edges to automatically spread apart to open said cover.

12. The cover as set forth in claim 2, wherein said front and rear walls are joined with said ribs on inner surfaces thereof, said cover thereafter being turned inside-out prior to use so that said ribs are external to said cover and through inherent spring force separate said walls at said opening.

13. A disposable self-opening cover system in combination with a drainable stoma pouch, said cover system comprising a cover having a front wall and a rear wall joined along respective bottom and side edges, unsealed upper edges of said walls defining an opening in said cover, each of said front and rear walls including at least one rib on a surface thereof adjacent said unsealed upper edges and causing said upper edges to be self-opening; and a self-locking clamping device for compressing the walls of said cover against said stoma pouch following insertion of an outlet spout within said opening, said self-locking clamping device sealingly pressing said front and rear walls of said cover against one another with said stoma pouch sandwiched therebetween across a full width thereof and without folding of either said stoma pouch or said cover to thereby seal a lower portion of said pouch above said outlet spout with said clamping device locked thereon and preventing escape of stoma pouch contents from said stoma pouch, said self-locking clamping device sealing said cover against said stoma pouch in a region below said ribs such that said ribs do not contribute to closure of said cover or said pouch but remain separated from one another, said cover, when so secured to the pouch by said clamping device, trapping any liquid or gases resident in said outlet spout.

14. The cover system as set forth in claim 13, wherein said front wall includes a first plurality of ribs and said rear wall includes a second plurality of ribs.

15. The cover system as set forth in claim 14, wherein said first plurality of ribs is opposed to said second plurality of ribs.

16. The cover system as set forth in claim 14, wherein said first plurality of ribs is vertically displaced relative to said second plurality of ribs.

17. The cover system as set forth in claim 16, wherein said rear wall includes a lip portion extending above at least a portion of the unsealed upper edge of said front wall, said second plurality of ribs being affixed to said lip portion.

18. The cover system as set forth in claim 13, wherein said ribs loop over the side edges to extend from the front wall to the rear wall, thereby causing the unsealed upper edges to automatically spread apart to open said cover.

19. The cover system as set forth in claim 13, wherein said cover is fabricated with said ribs on inner surfaces of said front and rear walls and is thereafter turned inside-out prior to use so that said ribs are external to said cover and through inherent spring force separate said walls at said opening.

20. A method of sealing a drainable stoma pouch, having a stoma opening and a tail section with an outlet spout, using a disposable self-opening cover and a clamping device, said cover having front wall and a rear wall joined along respective bottom and side edges, unsealed upper edges of said walls defining an opening, each of said front and rear walls including at least one rib on an external surface thereof to facilitate opening of said upper edges, which comprises the steps of:
  squeezing the ribs of said cover toward one another to expand a breadth of said opening;
  sliding the cover over the outlet spout of said stoma pouch and sufficiently upward in a direction toward the stoma opening so that a portion of said tail section extends within said cover and below said ribs; and
  clamping the walls of said cover against said tail section at a point below said ribs.

21. The cover as set forth in claim 1, wherein said cover is attached to said stoma pouch only by said clamping device.

22. A disposable cover for a drainable stoma pouch comprising a front wall and a rear wall joined along respective bottom and side edges, unsealed upper edges of said walls defining an opening for receiving an outlet spout of a stoma pouch, each of said front and rear walls having at least one rib on a surface thereof adjacent said unsealed upper edges, said ribs looping over the side edges to extend from the front wall to the rear wall and thereby causing the unsealed upper edges to be self-opening, and a clamping device for securing the walls of said cover to said stoma pouch following insertion of an outlet spout within said opening, said clamping device pressing said front and rear walls against one another to contain liquid and gases emitted from the stoma pouch within the cover.

* * * * *